(12) United States Patent
Joshi et al.

(10) Patent No.: US 7,227,039 B2
(45) Date of Patent: *Jun. 5, 2007

(54) RS 1-{4-[2-(ALLYLOXY)-ETHYL]PHENOXY}-3-ISOPROPYLAMINO PROPAN-2-OL, PROCESS FOR PREPARATION THEREOF AND PROCESS FOR PREPARATION OF RS BETAXOLOL

(75) Inventors: Ramesh Anna Joshi, Maharashtra (IN); Muthukrishnan Murugan, Maharashtra (IN); Dinesh Ramesh Garud, Maharashtra (IN); Sanjay Pandurang Borikar, Maharashtra (IN); Mukund Keshav Gurjar, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 317 days.

This patent is subject to a terminal disclaimer.

(21) Appl. No.: 10/978,896

(22) Filed: Nov. 1, 2004

(65) Prior Publication Data

US 2006/0094903 A1 May 4, 2006

(51) Int. Cl.
C07C 213/00 (2006.01)
(52) U.S. Cl. .................................... 564/349
(58) Field of Classification Search ................. 564/349
See application file for complete search history.

(56) References Cited

U.S. PATENT DOCUMENTS 5,731,463 A * 3/1998 Wang et al. ................. 564/399

6,989,465 B1 * 1/2006 Joshi et al. ................. 564/349

* cited by examiner

Primary Examiner—Peter O'Sullivan
(74) Attorney, Agent, or Firm—Morgan & Finnegan, LLP

(57) ABSTRACT

The present invention relates to RS 1-{4-[2-(allyloxy)-ethyl]phenoxy}-3-isopropylamino propan-2-ol of the formula (1), process for preparation thereof by selective allylation of p-hydroxy phenyl ethanol and use thereof in a preparation of RS betaxolol of formula (2)

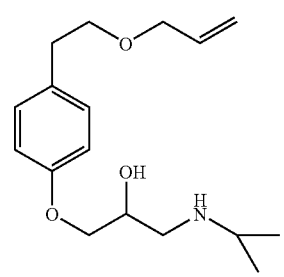

Formula (1)

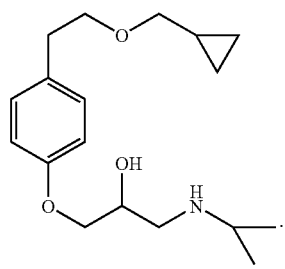

Formula (2)

11 Claims, No Drawings

RS 1-{4-[2-(ALLYLOXY)-ETHYL]PHENOXY}-3-ISOPROPYLAMINO PROPAN-2-OL, PROCESS FOR PREPARATION THEREOF AND PROCESS FOR PREPARATION OF RS BETAXOLOL

FIELD OF THE INVENTION

The present invention relates to RS 1-{4-[2-(allyloxy)-ethyl]phenoxy}-3-isopropylamino propan-2-ol of the formula (1), process for preparation thereof and use thereof in a preparation of RS betaxolol of formula (2) More particularly the present invention relates to the preparation of RS 1-{4-[2-(allyloxy)-ethyl]phenoxy}-3-isopropylamino propan-2-ol by selective allylation of p-hydroxy phenyl ethanol.

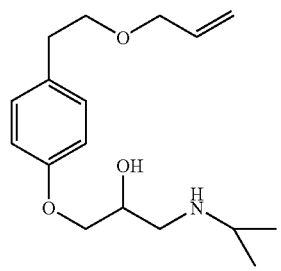

Formula (1)

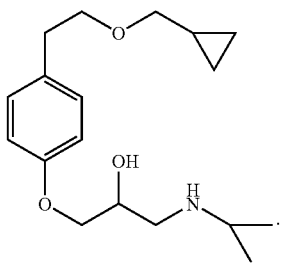

Formula (2)

BACKGROUND OF THE INVENTION

Racemic betaxolol of formula (2) is a β-adrenoreceptor antagonist with a pharmacological and pharmacokinetic profile for the treatment of chronic cardiovascular diseases like glaucoma. The disease glaucoma is characterized by progressive damage to the optic nerve caused by the increased pressure within the eye. Glaucoma is a serious disease of the eye, which may lead to the loss of peripheral vision and if untreated total blindness.

β-adrenoreceptor antagonist (β-blockers) are popularly used to lower intraoccular tension, other conditions of increased intraoccular pressure and management of essential hypertension. The principle effect of β-adrenoreceptor blocker is to reduce cardiac activity by diminishing or preventing β-adrenoreceptor stimulation i.e. by reducing the rate and force of contraction of the heart.

The processes employed for the preparation of betaxolol in the art involve protecting the phenol functional group so that the alcohol functionality can be alkylated. The resulting protection and deprotection steps extend the length of synthesis.

Manoury et al., (U.S. Pat. No. 4,252,984) describes the preparation of betaxolol which involves the benzylation of the phenolic alcohol of 4-hydroxyphenethanoic acid. The ester group is then reduced to alcohol and then condensation of 2-(4-benzyloxyphenyl)ethanol with cyclopropyl methyl halide to yield cyclopropyl methyl2-(4-benzyloxyphenyl) ether. It is then debenzylated and treated with epichlorohydrin to yield the compound, which on treatment with isopropylamine gives the betaxolol.

In another U.S. Pat. No. 4,760,182 by Ippolito et al., 4-hydroxyphenethanol is converted to a phenoxide anion with a base and then reacting it with epichlorohydrin to yield 1-(4-(2-hydroxyethyl)phenoxy)2,3-epoxypropane.

Wang et al., (U.S. Pat. No. 5,731,463) describes selective alkylation of the 4-hydroxy phenethanol via an oxygen dianion to produce intermediate which on reaction with epichlorohydrin and subsequent addition of isopropylamine produces the end product betaxolol.

In all the above processes cyclopropylmethyl halide has been employed for introducing cyclopropyl group as a reactive intermediate. The cyclopropylmethyl halide, is expensive, highly lachrymetric and unstable. These limitations make the reported processes economically unviable and difficult to scale up.

Therefore it is necessary to develop a short, simple, an economically viable alternative process for RS betaxolol wherein the use of cyclopropylmethyl halide is avoided, and steps involving protection and deprotection are avoided.

OBJECTS OF INVENTION

The object of present invention therefore is to provide a process for preparation of RS betaxolol. Another object is to avoid use of highly lachrymetric and unstable cyclopropylmethyl halide and also to avoid lengthier steps involving protection and deprotection of phenolic hydroxy group.

SUMMARY OF THE INVENTION

The above objects are fulfilled by providing a novel RS 1-{4-[2-(allyloxy)-ethyl]phenoxy}-3-isopropylamino propan-2-ol compound of formula (1), process for preparation thereof and use thereof in preparation of RS betaxolol of formula (2).

Accordingly, the present invention firstly provides RS 1-{4-[2-(allyloxy)-ethyl]phenoxy}-3-isopropylamino propan-2-ol of the formula 1

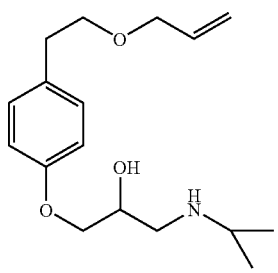

Formula (1)

or an acid salt thereof

The present invention also provides a process for the preparation of RS 1-{4-[2-(allyloxy)-ethyl]phenoxy}-3-isopropylamino propan-2-ol of the formula 1 or an acid salt thereof Formula (1)

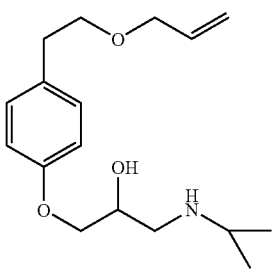

which comprises:
a) selectively allylating 2-(4-hydroxyphenyl)-ethanol of formula 3 with a base and an organic solvent to give 4-(2-allyloxy-ethyl)-phenol of formula 4;

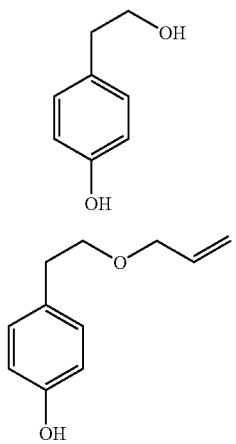

b) O-Alkylating 4-(2-allyloxy-ethyl)-phenol of formula 4 by treating with epichlorohydrin in the presence of an alkali to obtain a mixture of compounds of formulae 5 and 6

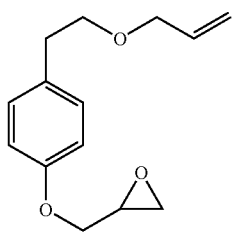

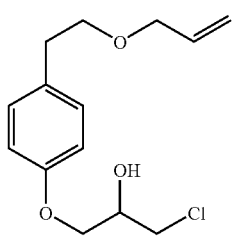

c) treating the mixture of compounds of formulae 5 and 6 with isopropyl amine to give 1-[4-(2-allyloxy-ethyl]-phenoxy)-3-isopropylamino-propan-2-ol of the formula 1;

d) and if desired, converting compound of formula 1 into an acid salt thereof by treating it with a corresponding acid.

In one of embodiment of the invention, the base used in step (a) is selected from the group consisting of sodium hydride or potassium t-butoxide.

In another embodiment of the invention, the solvent used in step (a) is an ethereal solvent comprising of tetrahydrofuran or a polar solvent selected from the group consisting of DMSO and DMF.

In still another embodiment of the invention, the alkali used in step (b) is an alkali hydroxide selected from the group consisting of sodium hydroxide and potassium hydroxide.

In another embodiment of the invention, the compound of formula 1 is treated with hydrochloric acid to obtain a hydrochloride of formula 8

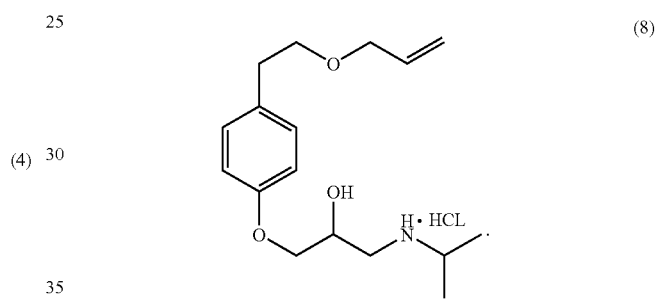

In another embodiment of the invention, the compound of formula 1 is treated with maleic acid to give maleate of formula 7

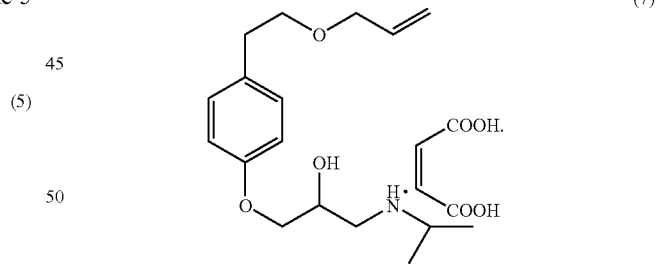

In another embodiment of the invention, the conversion of the compound of formula 1 to its hydrochloride salt of formula 8 is carried out in the presence of a solvent selected from a hydrocarbon selected in turn from the group consisting of toluene and cyclohexane, ethers selected in turn from the group consisting of diethyl ether and diisopropyl ether; alcohols selected in turn from the group consisting of ethanol, methanol and isopropanol.

In another embodiment of the invention, the conversion of the compound of formula 1 to its maleate salt of formula 7 is carried out in the presence of an ethereal solvent selected from the group consisting of diisopropyl ether and diethyl ether.

The present invention also provides a process for the preparation of a betaxolol of formula 2 from RS 1-{4-[2-(allyloxy)-ethyl]phenoxy}-3-isopropylamino propan-2-ol of the formula 1

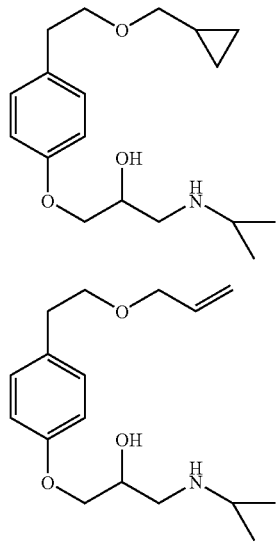

comprising cyclopropanating compound of formula 1 to obtain the racemic betaxolol of formula 2.

In another embodiment cyclopropanation of compound of formula 1 is carried out with diiodomethane in presence of Zn—Cu couple (Simmons Smith Reaction) or diethyl zinc in hexane (Furukawa modification).

DETAILED DESCRIPTION OF THE INVENTION

The present invention provided RS 1-{4-[2-(allyloxy)-ethyl]phenoxy}-3-isopropylamino propan-2-ol of the formula (1), process for preparation thereof and use thereof in preparation of RS betaxolol of formula (2).

Formula (1)

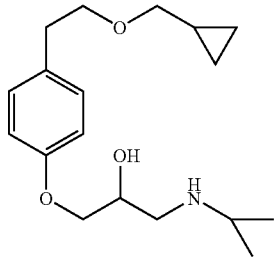

Formula (2)

The general process involved in the preparation of compound of formula 1 and its subsequent conversion to compound of formula 2 is given in the reaction scheme on the following page. The process of the invention broadly comprises (a) selectively allylating 2-(4-hydroxyphenyl)-ethanol of formula (3) with a base and an organic solvent to give 4-(2-allyloxy-ethyl)-phenol of formula (4);

(b) O-Alkylating 4-(2-allyloxy-ethyl)-phenol of formula (4) by treating with epichlorohydrin in the presence of an alkali to obtain the mixture of compounds of the formulae (5 and 6). Treating the mixture of compounds of the formulae (5 and 6) with isopropyl amine to give 1-[4-(2-allyloxy-ethyl]-phenoxy)-3-isopropylamino-propan-2-ol of the formula (1).

(c) Treating 1-{4-[2-(allyloxy)-ethyl]phenoxy}-3-isopropylamino propan-2-ol of the formula (1) with hydrochloric acid in IPA to give hydrochloride of formula (8).

(d) Treating 1-{4-[2-(allyloxy)-ethyl]phenoxy}-3-isopropylamino propan-2-ol of the formula (1) with maleic acid in ether to give maleate of formula (7).

The compound of formula 1 is then cyclopropanated by conventional methods such as Simmon-Smith reaction or Furukawa modification to obtain racemic betaxolol of formula 2.

The base used in step (a) can be sodium hydride or potassium t-butoxide and the solvent used in step (a) can be an ethereal solvent such as tetrahydrofuran or a polar solvent such as DMSO, DMF. In step (b) the alkali used is an alkali hydroxide such as sodium hydroxide or potassium hydroxide.

The solvent used for the preparation of hydrochloride salt of compound of formula 1 is either a hydrocarbon such as toluene or cyclohexane; ether such as diethyl ether or diisopropyl ether; or an alcohol such as ethanol, methanol or isopropanol. The solvent used for preparing the maleate salt of compound of formula 1 is an etheral solvent such as diisopropyl ether or diethyl ether.

SCHEME

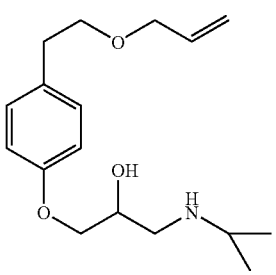

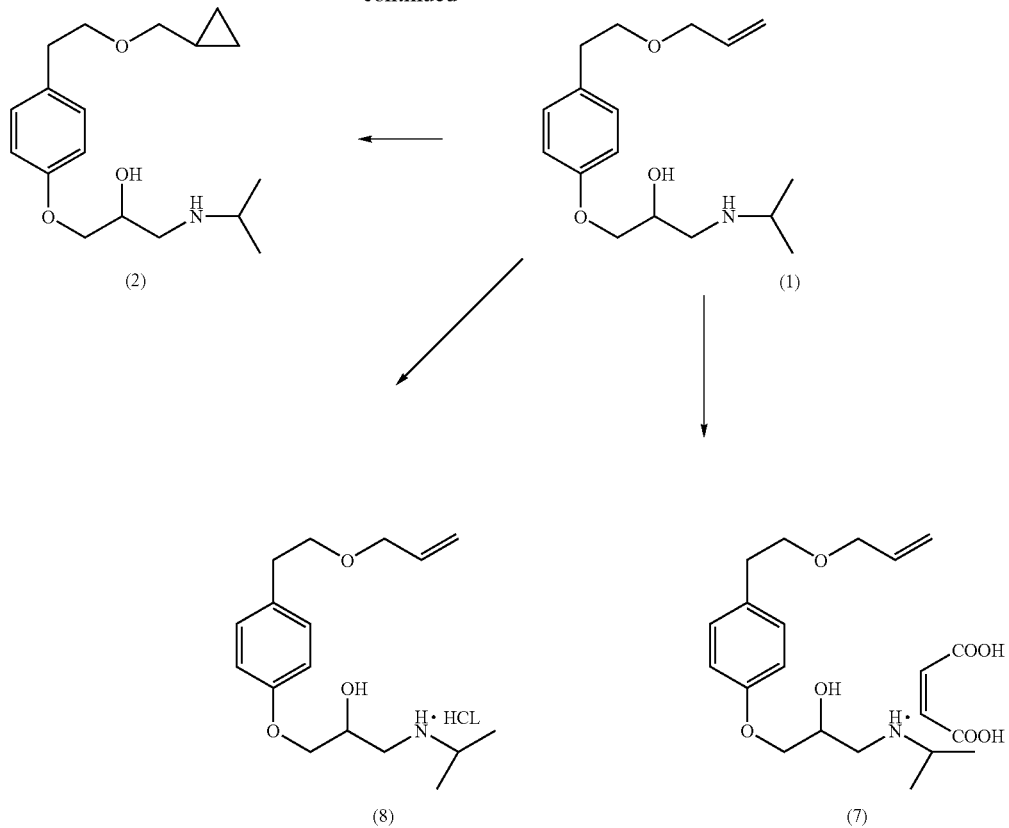

The cyclopropanation in step (c) may be carried out with diiodomethane in presence of Zn—Cu couple (Simmons Smith) or diethyl zinc in hexane. (Furukawa modification) to obtain RS betaxolol of formula (2).

The process of the present invention is described herein below with reference to the following examples, which are illustrative and should not be construed to limit the scope of the present invention in any manner.

EXAMPLE-1

This example describes the preparation of 4-[(2-Allyloxy)-ethyl)]-phenol of formula (4)

A reaction flask was charged with 4-hydroxy phenethyl alcohol of formula (3) (5 g, 0.036 mol), potassium t-butoxide (12.17 g, 0.10 mol) and 20 ml of DMSO. The mixture was stirred under nitrogen at 50° C. for 30 minutes. A solution of allyl chloride (3.00 ml, 0.036 mol) was added dropwise to the reaction mixture at room temperature and further stirred for 50 min. The reaction mixture was subsequently quenched with 40 ml of water. The aqueous mixture was washed three times with 10 ml portions of toluene to remove impurities. The product was extracted from neutralized aqueous mixture with toluene. The toluene extract was then washed with water and concentrated under vacuum to afford the compound of formula (4) as oil (3.07 g, 48%). The characterization of the product was done by $^1$H NMR and the results are mentioned hereinbelow.

$^1$H NMR: 2.87 (t, 2 H, $CH_2$—C); 3.64 (t, 2 H, $CH_2$—O); 4.02 (d, 2 H, $CH_2$—CH=$CH_2$; 5.20, 5.30 (dd, 2 H, olefinic); 5.94 (m, 1 H, olefinic); 6.74, 7.07 ($A_2B_2$, 4 H, aromatic)

EXAMPLE-2

This example describes the preparation of 2-[4-(2-allyloxy-ethyl)-phenoxymethyl]-oxirane of formula (5)

To the solution of aromatic phenol of formula (4) (2.83 g, 0.016 mol) in a mixture of acetone: water (4:1) was added sequentially NaOH (0.63 g, 0.016 mol), epichlorohydrin (6.21 g, 0.079 mol) and the reaction mixture was stirred under reflux for 2 hours, the mixture was concentrated and the residue partitioned between ethyl acetate and water. The organic layer was dried over anhydrous sodium sulphate, filtered and concentrated. The crude product was purified by silica gel chromatography using ethyl acetate and pet ether (1:9) as an eluent to afford compound of formula (5) (2.79 g 75%) as oil.

$^1$H NMR: 2.7–2.9 (m, 4 H, $CH_2$—C, $CH_2$—O); 3.64 (t, 2 H, $CH_2$—O); 3.75 (m, 1 H, $CH_2$—O); 4.02 (m, 3 H, $CH_2$—CH=$CH_2$, $CH_2$—O); 4.16 (dd, 1 H, $CH_2$—O); 5.20, 5.30 (dd, 2 H, olefinic); 5.94 (m, 1 H, olefinic); 6.84, 7.14 ($A_2B_2$, 4 H, aromatic).

EXAMPLE-3

This example describes the preparation of 1-{4-[2-(allyloxy)-ethyl]phenoxy}-3-isopropylamino propan-2-ol of formula (1)

A solution of the compound of formula (5) (3.70 g, 0.016 mol), isopropyl amine (7.46 ml, 0.127 mol) in methanol (20 ml) was stirred under reflux for 2 hours and then concentrated. The residue was partitioned between chloroform and water. The organic layer was dried over anhydrous sodium sulphate, filtered and concentrated. The residue was crystallized from pet ether to afford compound of formula (1) as a white solid 3.47 g (75%) mp 52–53° C.

$^1$H NMR: 1.08, 1.09 (2 S, 6 H, (CH$_3$)$_2$N); 2.69 (m, 1 H, CH—CH$_3$); 2.73–2.93 (m, 7 H, CH$_2$—C, CH$_2$—O, N—H, O—H, N—CH); 3.61 (t, 2 H, O—CH$_2$); 3.92–4.00 (m, 4 H, CH$_2$—O); 4.07 (m, 1 H, CH—OH); 5.20, 5.30 (dd, 2 H, olefinic); 5.94 (m, 1 H, olefinic); 6.85, 7.16 (A$_2$B$_2$, 4 H, aromatic). Mass: M$^+$=293.

EXAMPLE-4

This example describes the preparation of maleate salt of 1-{4-[2-(allyloxy)-ethyl]phenoxy}-3-isopropylamino propan-2-ol of formula (7)

Compound of formula (1) (4 g, 0.014 mol) was dissolved in ether (25 ml) to this maleic acid (1.43 g, 0.012 mol) was added and stirred for 1 hr. Filtered the white solid, which was maleate salt of formula (7) (4.75 g, 85%) mp 71° C.

EXAMPLE-5

This example describes the preparation of hydrochloride salt of 1-{4-[2-(allyloxy)-ethyl]phenoxy}-3-isopropylamino propan-2-ol of formula (8)

To a solution of compound of formula (1) (2.50 g) in 15 ml of toluene, isopropanol-HCl (1 eq) (5 ml) was added drop wise under nitrogen atmosphere with stirring (untill pH=2). The reaction mixture was stirred for 1 h, concentrated and again 5 ml of toluene was added, stirring continued for 15 min. This process was repeated twice, finally solvent was removed completely and diethyl ether was added to precipitate the solid. Filtered under nitrogen atmosphere and dried to obtain the compound of formula (8) 2.42 g (86%) mp 101–104° C.

EXAMPLE-6

This Example Describes the Preparation of Betaxolol of Formula (2)

To a stirred solution of compound of formula (1) (1 g, 0.003 mol) in dry toluene (5 ml), diethylzinc (1.1 M solution in toluene, 14 ml, 0.017 mol) was added at 0° C. under nitrogen atmosphere followed by diiodomethane (1.38 ml, 0.017 mol). The reaction was stirred for 16 h at 0° C. and poured over cold aqueous solution of ammonium chloride. The organic layer was separated and the aqueous layer extracted repeatedly with toluene. The combined organic layer was washed with a solution of sodium thiosulphate, dried over anhydrous sodium sulphate, filtered and concentrated to yield racemic betaxolol of formula (2) 1.6 g (84%) mp 70 –72° C. as a white solid.

M$^+$=307.

$^1$H NMR: 0.20 (q, 2 H, cyp); 0.53 (q, 2 H, cyp); 1.07 (m, 1 H, cyp); 1.08, 1.09 (2 S, 6 H, (CH$_3$)$_2$N); 2.69 (m, 1 H, CH—CH$_3$); 2.85 (m, 4 H, CH$_2$—C, CH$_2$—O); 3.27 (d, 2 H, O—CH$_2$); 3.61 (t, 3 H, CH—O); 3.95 (d, 2 H, CH$_2$—O); 4 (m, 1 H, CH—OH); 6.85, 7.16 (A$_2$B$_2$, 4 H, aromatic).

We claim:

1. RS 1-{4-[2-(allyloxy)-ethyl]phenoxy}-3-isopropylamino propan-2-ol of the formula 1

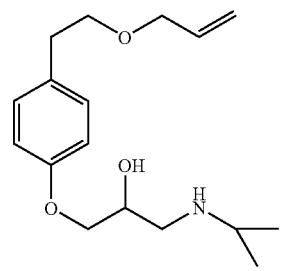

Formula (1)

or an acid salt thereof.

2. A process for the preparation of RS 1-{4-[2-(allyloxy)-ethyl]phenoxy}-3-isopropylamino propan-2-ol of the formula 1 or an acid salt thereof

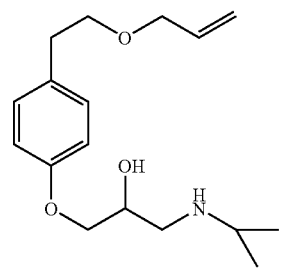

Formula (1)

which comprises:

(a) selectively allylating 2-(4-hydroxyphenyl)-ethanol of formula 3 with a base and an organic solvent to give 4-(2-allyloxy-ethyl)-phenol of formula 4;

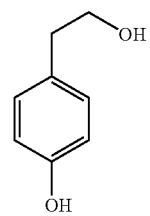

(3)

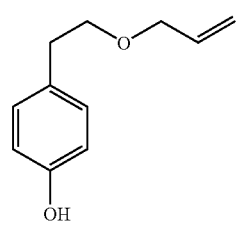

(4)

(b) O-Alkylating 4-(2-allyloxy-ethyl)-phenol of formula 4 by treating with epichlorohydrin in the presence of an alkali to obtain a mixture of compounds of formulae 5 and 6

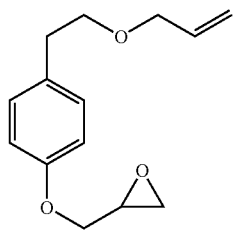
(5)

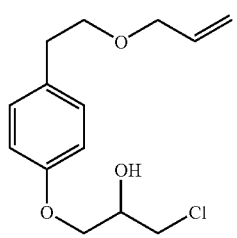
(6)

(c) treating the mixture of compounds of formulae 5 and 6 with isopropyl amine to give 1-[4-(2-allyloxy-ethyl-phenoxy)-3-isopropylamino-propan-2-ol of the formula 1;

(d) and if desired, converting compound of formula 1 into an acid salt thereof by treating it with a corresponding acid.

3. A process as claimed in claim 2 wherein the base used in step (a) is selected from the group consisting of sodium hydride or potassium t-butoxide.

4. A process as claimed in claim 2 wherein the solvent used in step (a) is an ethereal solvent comprising of tetrahydrofuran or a polar solvent selected from the group consisting of DMSO and DMF.

5. A process as claimed in claim 2 wherein the alkali used in step (b) is an alkali hydroxide selected from the group consisting of sodium hydroxide and potassium hydroxide.

6. A process as claimed in claim 2 wherein the compound of formula 1 is treated with hydrochloric acid to obtain a hydrochloride of formula 8

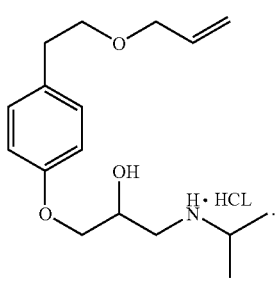
(8)

7. A process as claimed in claim 2 wherein the compound of formula 1 is treated with maleic acid to give maleate of formula 7

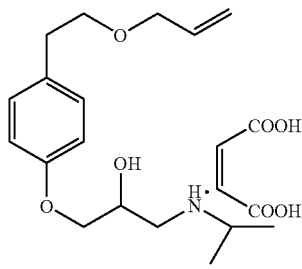
(7)

8. A process as claimed in claim 6 wherein the conversion of the compound of formula 1 to its hydrochloride salt of formula 8 is carried out in the presence of a solvent selected from a hydrocarbon selected in turn from the group consisting of toluene and cyclohexane, ethers selected in turn from the group consisting of diethyl ether and diisopropyl ether; alcohols selected in turn from the group consisting of ethanol, methanol and isopropanol.

9. A process as claimed in claim 7 wherein the conversion of the compound of formula 1 to its maleate salt of formula 7 is carried out in the presence of an ethereal solvent selected from the group consisting of diisopropyl ether and diethyl ether.

10. A process for the preparation of a betaxolol of formula 2 from RS 1-{4-[2-(allyloxy)-ethyl]phenoxy}-3-isopropylamino propan-2-ol of the formula 1

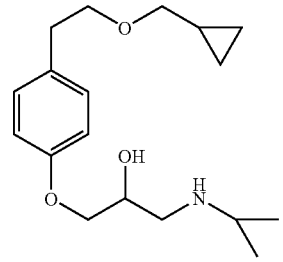
Formula (2)

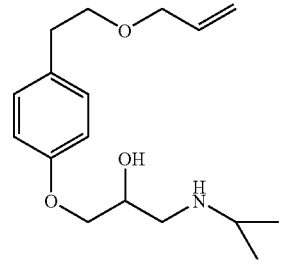
Formula (1)

comprising cyclopropanating compound of formula 1 to obtain the racemic betaxolol of formula 2.

11. A process as claimed in claim 10 wherein the cyclopropanation of compound of formula 1 is carried out with diiodomethane in presence of Zn—Cu couple (Simmons Smith Reaction) or diethyl zinc in hexane (Furukawa modification).

* * * * *